(12) United States Patent
Martin et al.

(10) Patent No.: US 6,186,229 B1
(45) Date of Patent: Feb. 13, 2001

(54) DOWNHOLE CONNECTOR FOR PRODUCTION TUBING AND CONTROL LINE AND METHOD

(75) Inventors: David G. Martin, Inverurie; Damien Patton, Aberdeen, both of (GB)

(73) Assignee: Baker Hughes Incorporated, Houston, TX (US)

( * ) Notice: Under 35 U.S.C. 154(b), the term of this patent shall be extended for 0 days.

(21) Appl. No.: 09/239,879

(22) Filed: Jan. 29, 1999

Related U.S. Application Data

(60) Provisional application No. 60/072,934, filed on Jan. 29, 1998.

(51) Int. Cl.[7] .................................................. E21B 47/00
(52) U.S. Cl. ...................................... 166/250.08; 166/375
(58) Field of Search ........................ 166/250.01, 250.08, 166/336, 337, 55, 377, 297, 373–375

(56) References Cited

U.S. PATENT DOCUMENTS

| | | | |
|---|---|---|---|
| 4,526,233 | * | 7/1985 | Stout ..................................... 166/377 |
| 5,323,853 | * | 6/1994 | Leismer et al. ......................... 166/55 |

FOREIGN PATENT DOCUMENTS

WO 97/29270 A1 * 8/1997 (WO).

* cited by examiner

Primary Examiner—Christopher J. Novosad
(74) Attorney, Agent, or Firm—Duane, Morris & Heckscher LLP

(57) ABSTRACT

A connector is disclosed to facilitate the testing of a control line or lines adjacent a bottomhole assembly. A running tool is connected to a lower portion of the connector which is, in turn, connected to the bottomhole assembly. The running tool allows testing of the control line adjacent the bottomhole assembly and thereafter, the operation of components of the bottomhole assembly. The running tool is removed and the upper portion of the string, including the mating portion of the connector at its lower end, is inserted into the wellbore. The connector components are self-aligning and lock to each other downhole to complete the production tubing and the control line tubing to the surface. Multiple control lines are envisioned between the surface and the bottomhole assembly. Multiple connectors can be used in a given production string, and provisions can be made for operation of a multiplicity of downhole components from the control line system which extends along the production tubing.

20 Claims, 10 Drawing Sheets

DOWNHOLE CONNECTOR FOR PRODUCTION TUBING AND CONTROL LINE AND METHOD

This application claims the benefit of U.S. Provisional Application No. 60/072,934, filed on Jan. 29, 1998.

FIELD OF THE INVENTION

The field of this invention relates to the make-up of bottomhole assemblies on a tubing string, in conjunction with one or more control lines extending from the surface to the bottomhole assembly, and methods for assembly and test of such systems.

BACKGROUND OF THE INVENTION

Control lines have been attached to production tubing for operation of a variety of downhole components. Typically, the control line is assembled to the production tubing for running into the well together. If rigid tubing is used, the production string is made-up to position the bottomhole assembly at the desired depth, in conjunction with the attachment of the control line or control lines. It is only when the bottomhole assembly is fully positioned at the desired location downhole that the integrity of the control line can be first tested. Thus, when the bottomhole assembly is finally positioned and the control line is tested and a problem arises, the entire production string up to the bottomhole assembly must be removed from the wellbore in an effort to determine where leakage has occurred. What has been lacking in these techniques is the ability to primarily position the bottomhole assembly at the desired location and test portions of the control line adjacent to the bottomhole assembly while the bottomhole assembly is in position downhole. Accordingly, one of the objects of the present invention is to allow the flexibility of testing the portion of the control line where leakage is most likely to occur, i.e., adjacent the bottomhole assembly, where there are more joints in the system.

Another objective of the present invention is to facilitate the assembly of a control line system which extends from the surface down to the bottomhole assembly and back up again along the production tubing to the surface. With such a layout, fiber optic technology can be used to insert, through the control line, a fiber optic cable which extends from the surface to the bottomhole assembly and back to the surface. The positioning of such a fiber optic cable in the control line allows well conditions to be monitored from the surface on a real-time basis. Thus, when a particular zone produces water and its temperature drops, the fiber optic cable can sense this occurrence and its position so that surface personnel can take appropriate corrective action. The control line connection system can be used for numerous other applications. This with a fiber optic cable is just one example of how a U-shaped control line can be used.

The objective of the connector of the present invention is to also allow as many branch connections as necessary so that multiple downhole devices can be operated as required. The connector also allows, through the use of a running tool, an opportunity to not only test the control line adjacent the bottomhole assembly, but also to operate certain components of the bottomhole assembly through the running tool, whereupon the running tool can be removed and the remainder of the string connected to the bottomhole assembly through the unique connector. These and other advantages will become more apparent to those of ordinary skill in the art from a review of the description of the connector and the method below.

SUMMARY OF THE INVENTION

A connector is disclosed to facilitate the testing of a control line or lines adjacent a bottomhole assembly. A running tool is connected to a lower portion of the connector which is, in turn, connected to the bottomhole assembly. The running tool allows testing of the control line adjacent the bottomhole assembly and thereafter, the operation of components of the bottomhole assembly. The running tool is removed and the upper portion of the string, including the mating portion of the connector at its lower end, is inserted into the wellbore. The connector components are self-aligning and lock to each other downhole to complete the production tubing and the control line tubing to the surface. Multiple control lines are envisioned between the surface and the bottomhole assembly. Multiple connectors can be used in a given production string, and provisions can be made for operation of a multiplicity of downhole components from the control line system which extends along the production tubing.

DETAILED DESCRIPTION OF THE PREFERRED EMBODIMENT

Figure 1A:
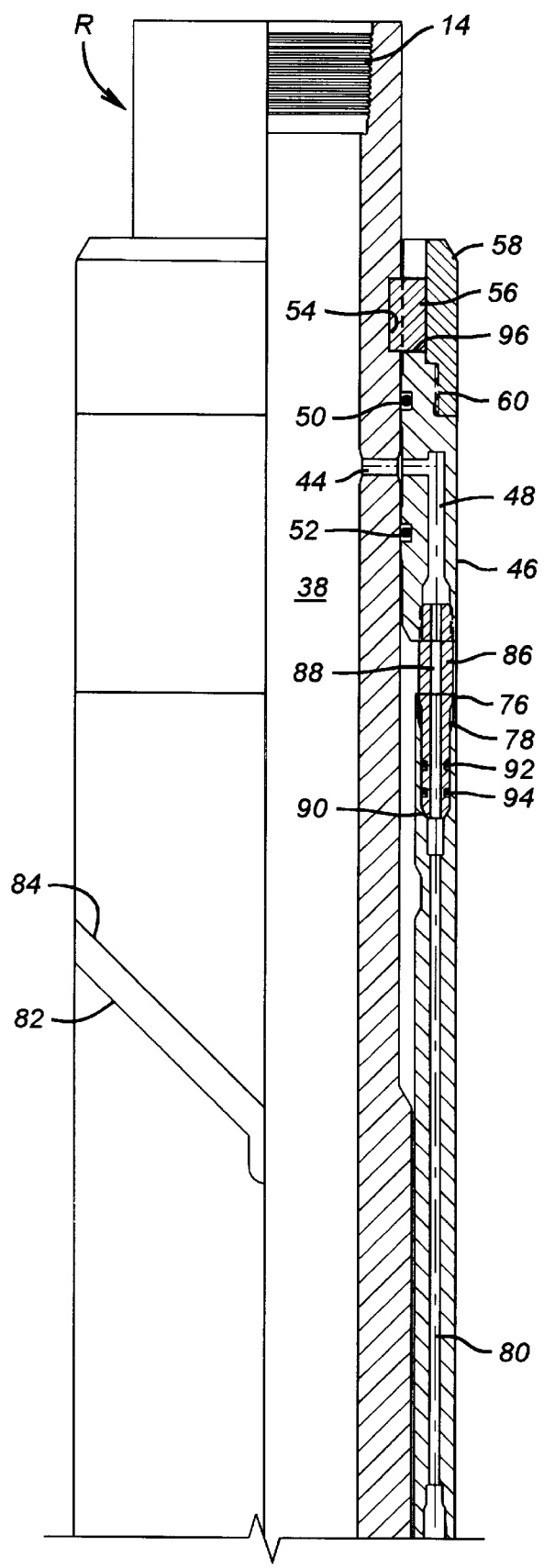
FIGS. 1a–c are a sectional elevational view of the outer or lower portion of the connector with the running tool inserted therein.
Figure 1B:
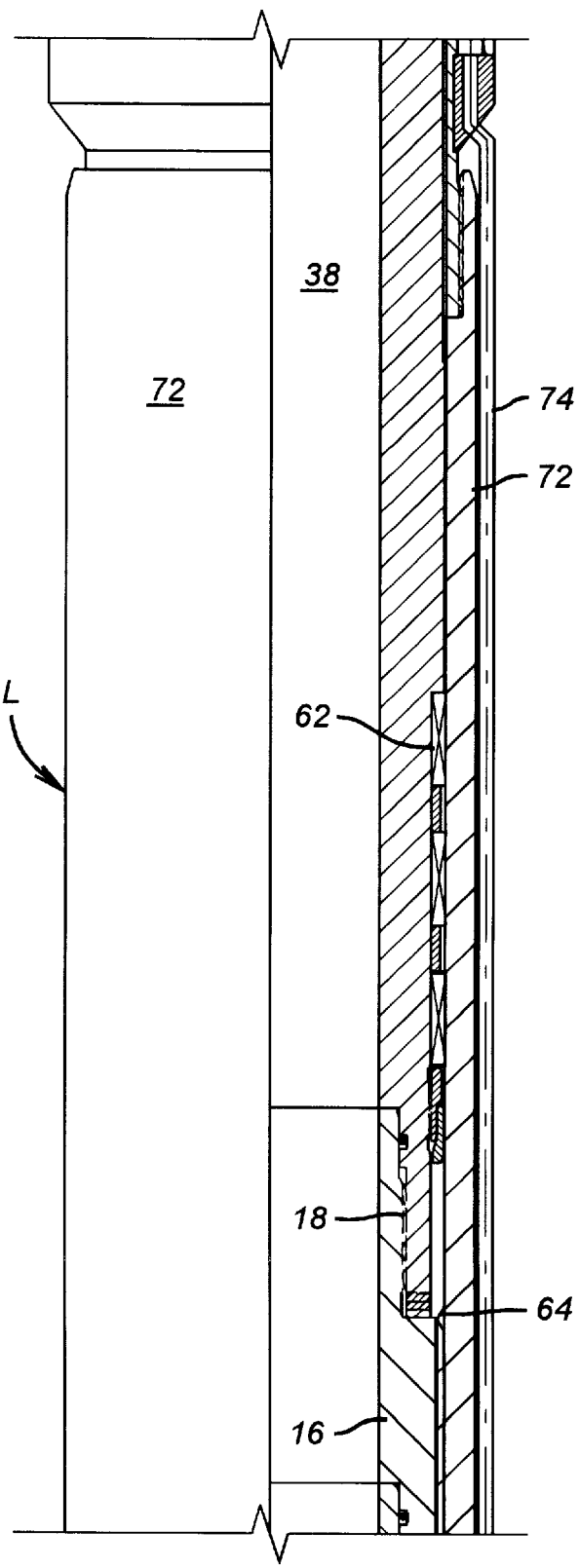
Figure 1C:
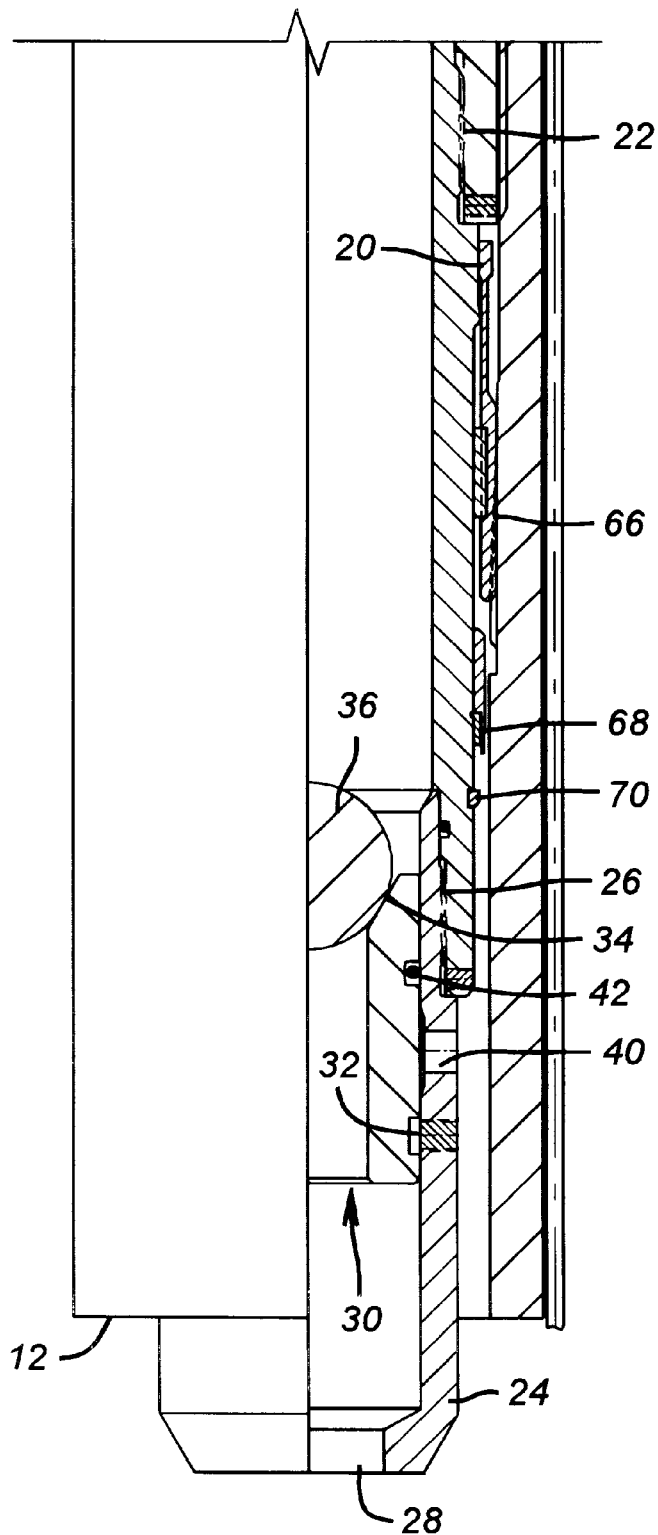

Referring to FIGS. 1a–c, the running tool R is shown fully inserted into the lower body L of the connector C. The lower body L has a thread 10 at its lower end 12, which is best seen in FIG. 2c. Thread 10 is connected to the bottomhole assembly, which is not shown. This bottomhole assembly can include packers, sliding sleeves, and other types of known equipment.

The running tool R is made up of a top sub 14, which is connected to a sleeve 16 at thread 18. Sleeve 16 is connected to sleeve 20 at thread 22. Sleeve 20 is connected to bottom sub 24 at thread 26. Bottom sub 24 has a bottom passage 28, as well as a ball seat assembly 30. The ball seat assembly 30 is held to the bottom sub 24 by shear pin or pins 32. Although a shear pin or pins 32 are shown, other types of breakable members can be employed without departing from the spirit of the invention. The ball seat assembly 30 has a tapered seat 34 to accept a ball 36 to build pressure in internal passage 38. Bottom sub 24 also has a lateral port 40 which, in the position shown in FIG. 1c, is isolated from the passage 38 by virtue of O-ring seal 42. Those skilled in the art will appreciate that during run-in, the ball 36 is not present. Accordingly, passage 38 has an exit at the passage 28 so that the bottomhole assembly, which is supported off the lower end of the lower body L, can be run in the hole while circulation takes place. Eventually, the bottomhole assembly is stabbed into a sump packer (not shown), which seals off the circulation through passage 38. It is at that time that the ball 36 can be dropped onto seat 34 to close off passage 38. At that time, O-ring 42 prevents leakage through the port 40, allowing pressure to be built up in passage 38 above the ball 36. This pressure can be communicated through a lateral port 44, as seen in FIG. 1a, into orientation sub 46. Orientation sub 46 has a passage which makes a right-angle turn 48 extending therethrough. Seals 50 and 52 prevent leakage between orientation sub 46 and the running tool R.

The running tool R also has a groove 54 to accept a dog 56 which is held in place by assembly of retaining cap 58, as will be described below. When retaining cap 58 is secured to orientation sub 46 at thread 60, with dog 56 in place in groove 54, the running tool R is locked in position with respect to orientation sub 46.

Looking further down the running tool R as shown in FIG. 1b, a seal assembly 62 encounters a seal bore 64 to seal between the lower body L and the running tool R. A locking ratchet assembly 66, of a type well-known in the art, is located toward the lower end of the running tool R. The ratchet teeth in a known manner allow the running tool R to advance within the lower body L but prevent removal unless a shear ring 68 is broken when contacted by a snap ring 70 after application of a pick-up force.

The lower body L includes a tubular housing 72 which, as previously stated, has a lower end 12 with a thread 10 for connection of the bottomhole assembly. In the preferred embodiment, a pair of control lines, only one of which 74 is shown, run longitudinally along the length of the tubular housing 72. The control line 74 terminates at an upper end 76 with a receptacle 78. In order to make the control line connection, the control line 74 becomes a passage 80 prior to the termination of passage 80 in the receptacle 78. Passage 80 is shown in alignment with passage 48. This occurs because when the running tool R is made up to the lower body L, preferably at the surface, an alignment flat 82 engages a similarly oriented alignment flat 84. Alignment flat 82 is on the housing 72, while alignment flat 84 is on communication crossover 86. The crossover 86 contains a passage 88 which is an extension of passage 48. Passage 88 terminates in a projection 90, which is sealed into the receptacle 78 by O-rings 92 and 94, which are mounted to the projection 90. Although O-rings 92 and 94 are shown, other sealing structures are within the scope of the invention. In essence, the receptacle 78 has a seal bore to accept the seals 92 and 94. The orientation of the opposed flats 82 and 84 ensure that the crossover 86 rotates to orient the projection 90 in alignment with receptacle 78 as the crossover 86 is advanced over the running tool R. To complete the assembly after proper alignment, the running tool R is firmly pushed into the lower body L so that the seal 62 engages seal bore 64, and the locking ratchet assembly 66 fully locks the running tool R to the lower body L. At this time, the crossover 86, which is made up over the running tool R and is now properly aligned, has its projection 90 progress into the receptacle 78. Thereafter, the projection 90 is fully advanced into a sealing relationship into the receptacle 78 so that its passage 48 is in alignment with port 44. This orientation is ensured by alignment of a window 96 in the orientation sub 46 with the groove 54 on the top sub 14 of the running tool R. When such an alignment is obtained, the dog 56 is pushed through window 96 so that it partially extends into the window and partially into groove 54. At that time, the retaining cap 58 is threaded onto thread 60 to secure the position of the dog 56, which, in turn, assures the alignment of port 44 with passage 48. The running tool R is now fully secured to the lower body L of the connection C. Rigid or coiled tubing can now be connected to the running tool R at thread 14.

The bottomhole assembly (not shown), which is supported off the lower end 12 of the body 72, can now be run into position in the wellbore while circulation continues through passage 38 and outlet 28. Ultimately, when the bottomhole assembly is stabbed into a sump packer, circulation ceases and a signal is thus given to surface personnel that the bottomhole assembly has landed in the desired position. At that time, the ball 36 is dropped against the seat 34, and pressure is built up in passage 38 above ball 36. This pressure communicates laterally through port 44 into passage 48 and, through the sealed connection of the projection 90 in the receptacle 78, the developed pressure communicates into the control line 74 to the bottomhole assembly. Since, in the preferred embodiment, there are actually a pair of control lines 74, there are multiple outlets 44 in the running tool R such that all the control lines 74 going down to the bottomhole assembly and making a U-turn and coming right back up adjacent the tubular housing 72 and terminating in a similar connection to that shown in FIG. 1a, are all pressure-tested simultaneously. If it is determined that there is a loss of pressure integrity in the control line system 74 at this point, the bottomhole assembly can be retrieved using the running tool R or alternatively, the running tool R can be released from the lower body L and the bottomhole assembly can be retrieved in a separate trip. If, on the other hand, the integrity of the control line system 74 is acceptable, pressure can be further built up in passage 38 to blow the ball 36, with the ball seat assembly 30, into the bottom of bottom sub 24 where they are both caught. As a result, the port 40 is exposed so that pressure can be communicated to the bottomhole assembly for operation of its components, such as a packer or a sliding sleeve valve, for example. Once the bottomhole assembly is completely functioned through the pressure applied at port 40, an upward force is applied to the running tool R to break the shear ring 68 so that the entire assembly of the running tool R, along with the orientation sub 46 and the crossover 86, can be removed. As this pick-up force is applied, the projection 90, which is a component of the crossover 86, comes out of the receptacle 78 so that each of the control lines 74 (only one being shown) becomes disconnected as the running tool R is moved out completely from the lower body L.

Figure 2A:
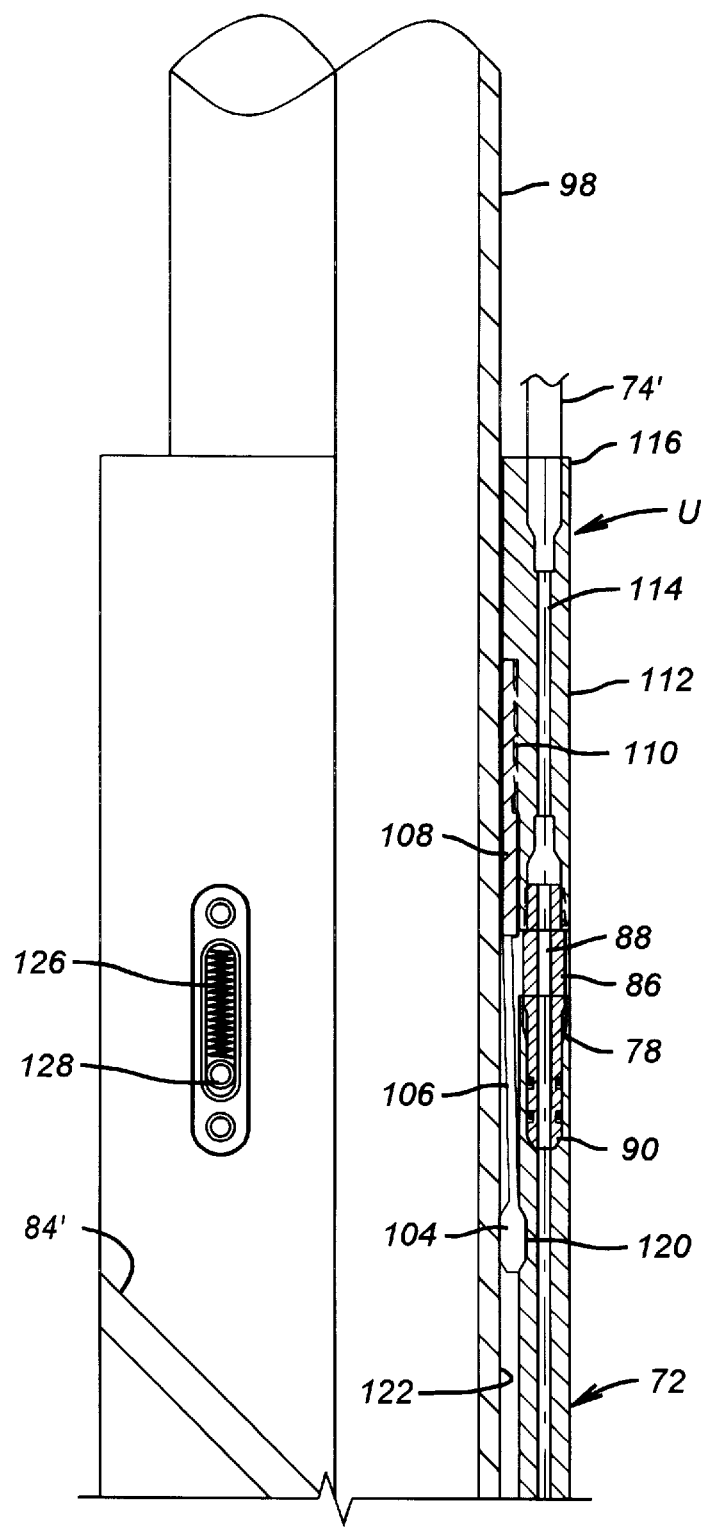
FIGS. 2a–c show both portions of the connector in sectional elevation connected to each other.

At this point the upper string 98, shown in FIG. 2a, which is connected to the upper body U, can be run in the wellbore for connection to the lower body L. Alternatively, the upper string 98 can be inserted at a much later time.

Figure 2B:
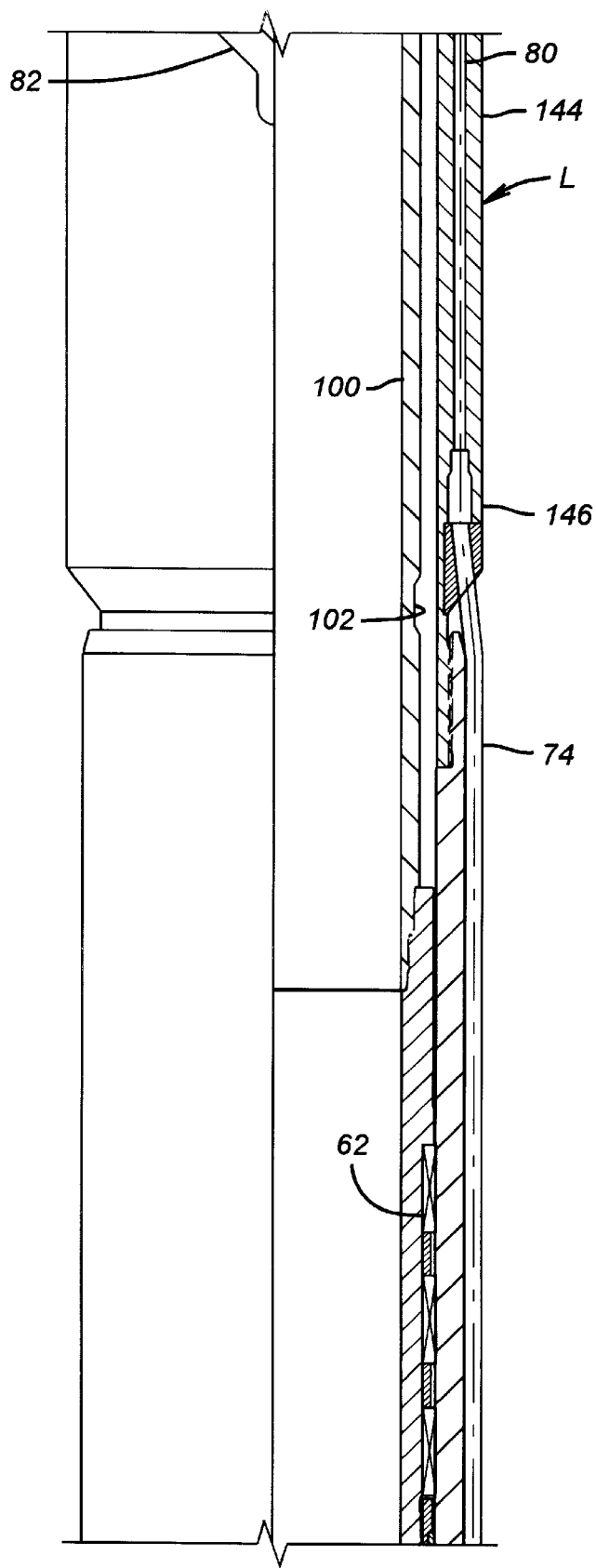
Figure 2C:
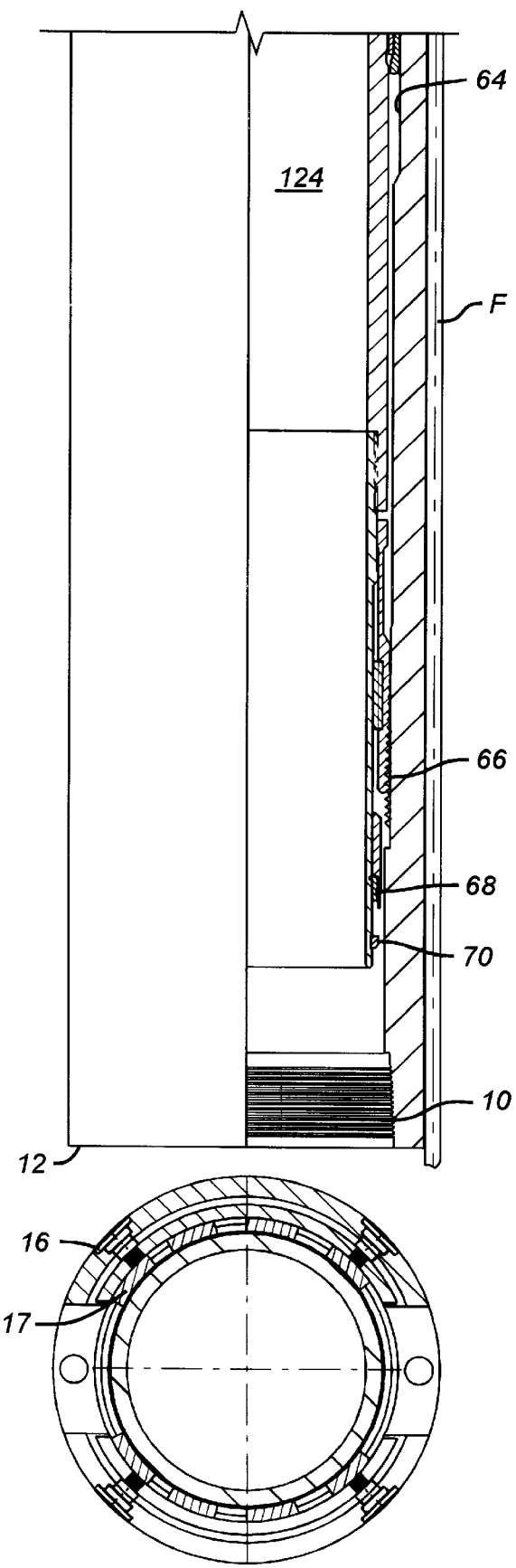
Figure 3A:
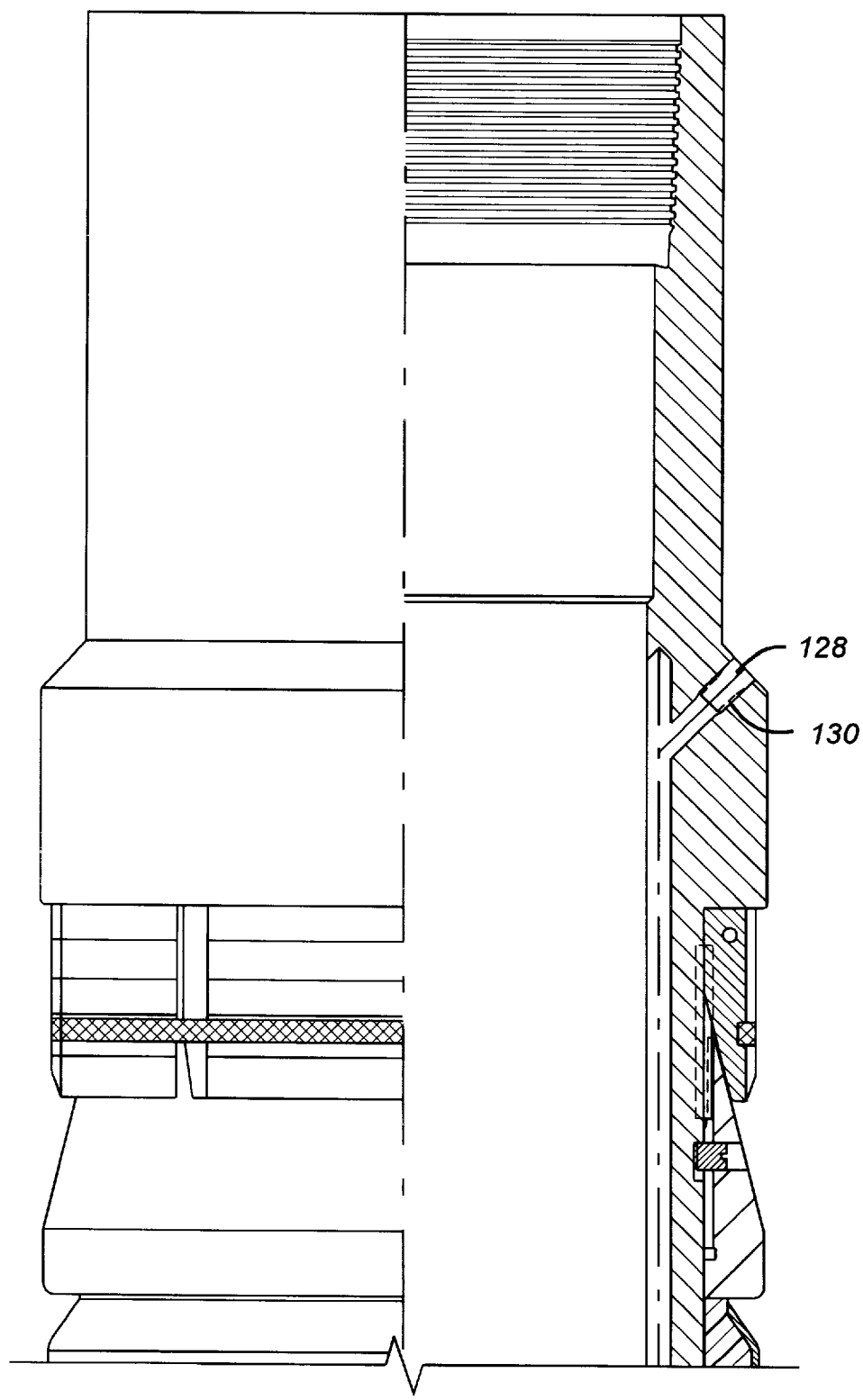
FIGS. 3a–d show a passage around a packer in sectional elevational view, indicating the path of the control line around the packer sealing and gripping assemblies.
Figure 3B:
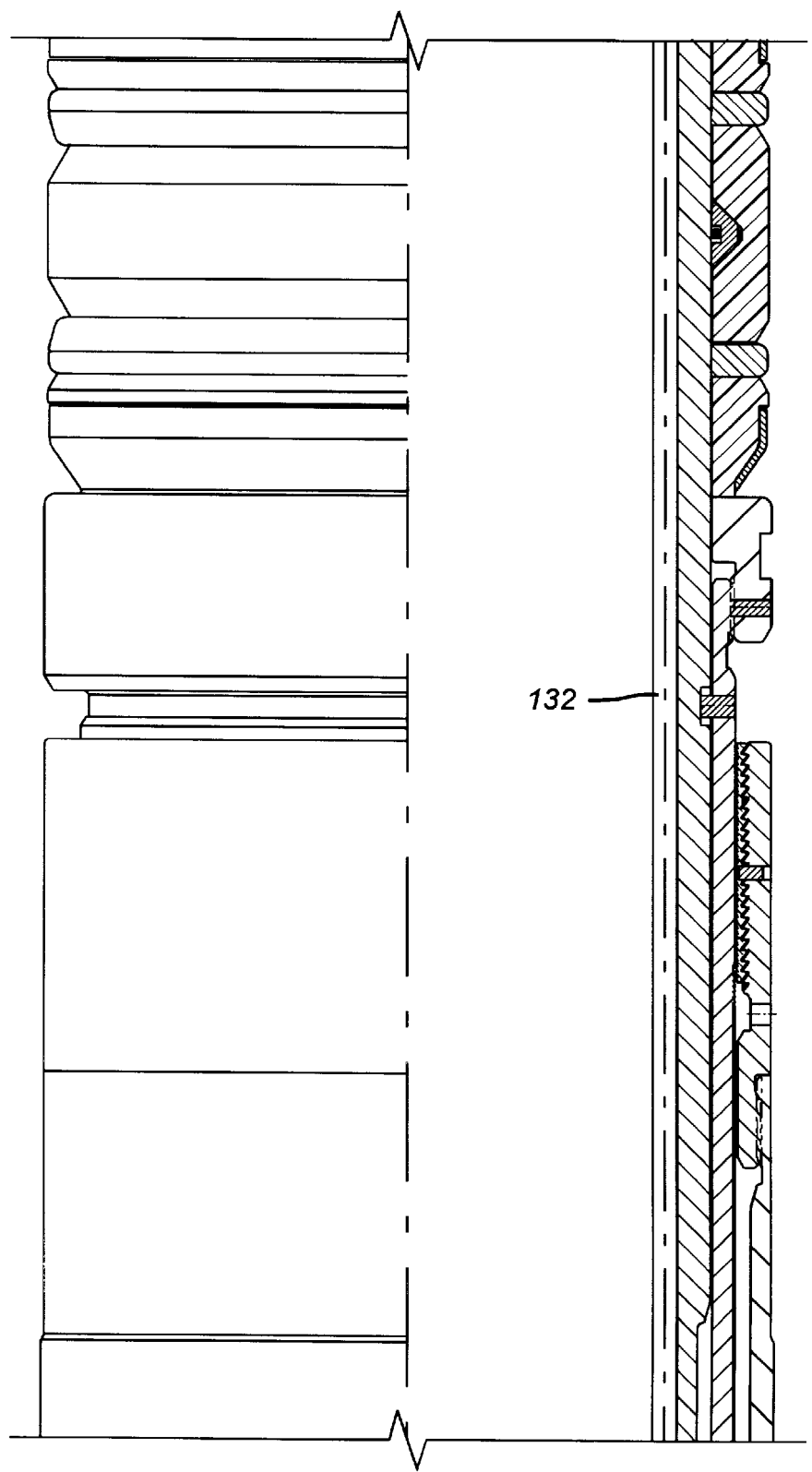
Figure 3C:
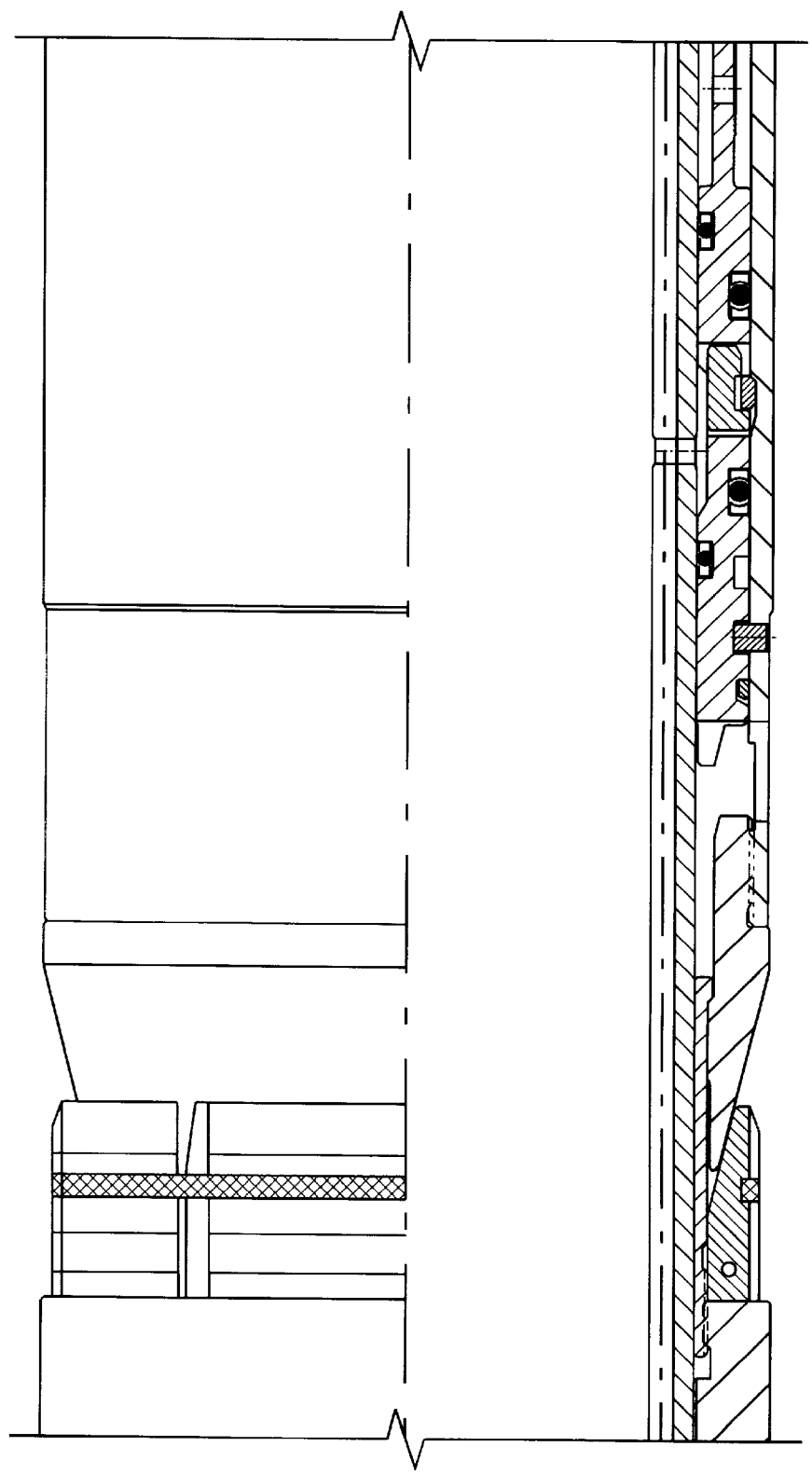
Figure 3D:
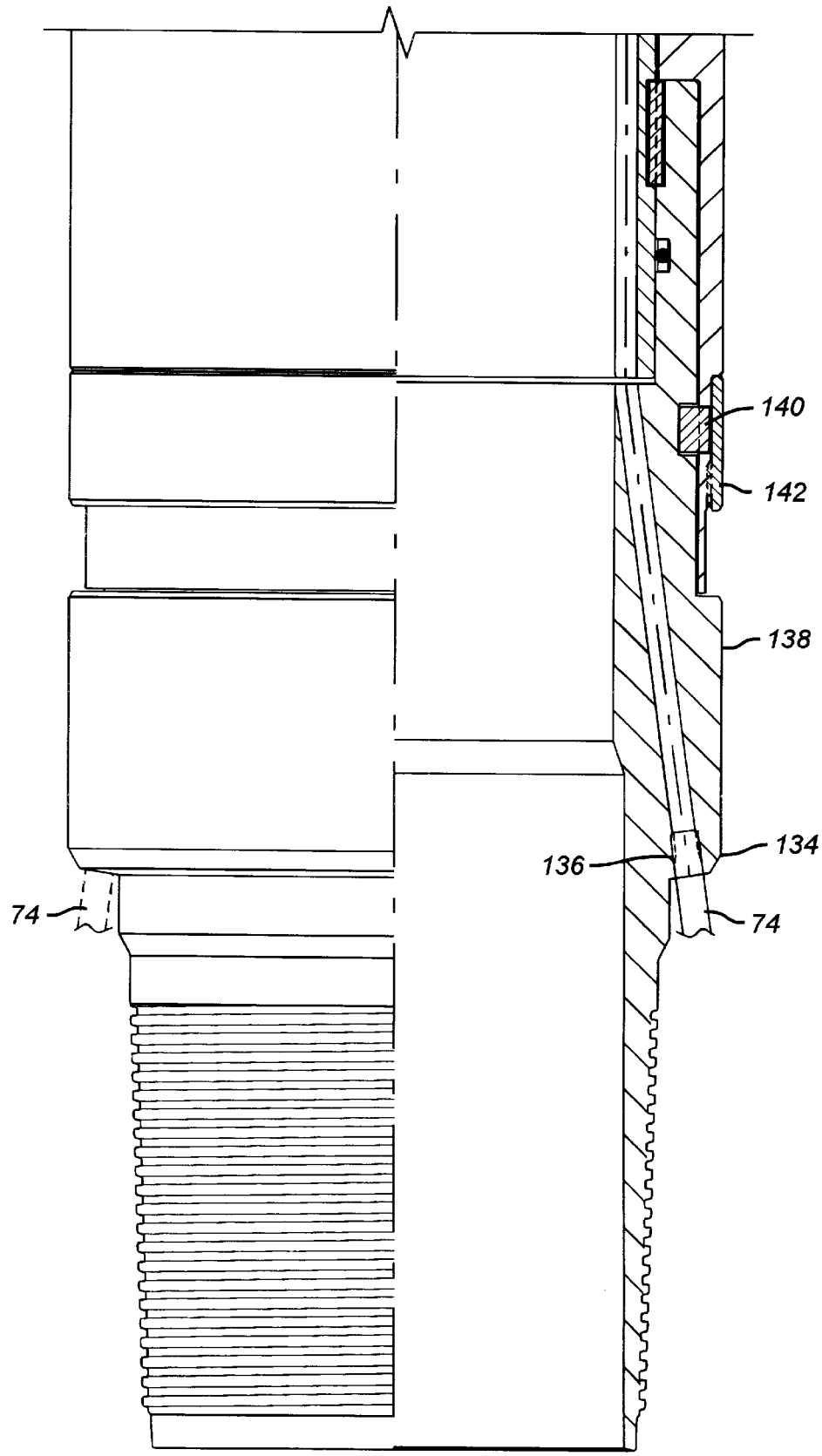

The upper body U has some constructional differences from the orientation sub 46 and the crossover 86 used in conjunction with the running tool R. Whereas the components 46 and 86 were assembled by hand at the surface, the counterpart components of the upper body U must connect automatically to the lower body L. Those skilled in the art will be appreciate that the view in FIGS. 2a–c is the view of the upper body U fully connected into the lower body L. However, there are certain components that are in a different position as the upper body U approaches the lower body L. The string 98 extends as a mandrel to support the upper body U and has numerous similarities to the running tool R which will not be repeated in great detail at this point. A seal assembly 62 contacts a seal bore 64, while a locking mechanism of the ratchet type 66 is employed in upper body assembly U, just as in the running tool R. Also present is a shear release in the form of an L-shaped ring 68, which for release is broken by a snap ring 70. The mandrel 100, which forms an extension of the upper string 98, includes an outer groove 102. During the initial run-in, a series of collet heads 104 is initially in alignment with groove 102. These collet heads 104 are held securely in groove 102 by sleeve 17 (shown in section in FIG. 2c). Sleeve 17 is pushed into this position by spring 126. The collet heads 104 extend from a series of long fingers 106, which in turn extend from a ring 108. Ring 108 is connected at thread 110 to orientation sub 112. Orientation sub 112 has a passage 114, including an upper end 116 which one of the accepts the control lines 74' which run from the surface to upper end 116 along the upper string 98. Again, it should be noted that a plurality of control lines 74 and 74' are contemplated so that when the upper body U is connected to the lower body L, more than one control line connection is made simultaneously. As previously stated, the control line from the surface 74' extends down to the upper end 116 and then becomes passage 114. A crossover 86 has a passage 88 which is in alignment with passage 114. As before, the alignment flat 82 on the tubular housing 72 engages an alignment flat 84' on the crossover 86. However, rotational movement about the longitudinal axis is still possible while the collet heads 104 are longitudinally captured in groove 102. This ability to rotate while longitudinally trapped allows the mating flats 82 and 84' to obtain the appropriate alignment so that ultimately, passage 80 can be connected to passage 88 as the projection 90 enters the receptacle 78, as described above. As this is occurring, the groove 102, with the collet heads 104 longitudinally trapped to it, comes into alignment with groove 120, thus allowing the collet heads 104 to enter groove 120 and subsequently become locked in groove 120 as a result of opposing surface 122. This is precisely the position shown in FIGS. 2a and 2b. Thus, as the connection is firmly made up connecting passage 114 to passage 80 by virtue of a sealed connection between the projection 90 and the receptacle 78, that position is locked into place as collet heads 104 become trapped against longitudinal movement into groove 120 which is on the tubular housing 72 of the lower body L. It is at that time that further longitudinal advancement of the upper string 98 allows the seal 62 to enter the seal bore 64 and ultimately the locking assembly 66 to secure the mandrel 100 to the lower housing 72. Thus, with seal assembly 62 functional, production can take place through the passage 124 in the mandrel 100. The seal assembly 62 in effect prevents leakage between the mandrel 100 and the tubular housing 72, which is a part of the lower body L.

When disconnecting, collet 104 drops into groove 102, and the connection alignment sub 112 and housing 72 start to move apart. To ensure the collet 104 remaining in the groove 102, sleeve 17 (shown in section in FIG. 2c) is pushed over the collet 104 by spring 126, locking it in place in the groove 102. The reverse procedure happens when reconnecting.

As shown in FIG. 2c, the control line 74 extends beyond the lower end 12 and can extend through a packer as illustrated in FIGS. 3a–d. The control line 74 is literally inserted into opening 128 and secured in place with a jam nut (not shown) threaded into threads 130. The control line 74 extends through a passage 132 and emerges out at lower end 134, where a jam nut (not shown) is secured to threads 136. To facilitate manufacturing, the lower end of the passage 132 extends through a sleeve 138. The passage through the sleeve 138 is aligned with the main passage 132 and the aligned position is secured by a dog 140, which is locked in position by a ring 142. Also shown in FIG. 3d in dashed lines is the return control line from the bottomhole assembly going back up to the surface, which passes through the packer shown in FIGS. 3a–d in a similar manner and preferably at 180° to the passage 132 which is illustrated in the part sectional view. The control line 74 shown in dashed lines comes back up into the lower body L and is connected to the upper body U in the manner previously described.

Those skilled in the art will appreciate that what has been shown is a simple way to test the control line 74 adjacent the bottomhole assembly without running the upper string 98 with its attendant control line segments. Once the lower portion of the control line 74 has been tested and determined to be leak-free, the running tool R illustrated in FIGS. 1a–c can be used to set downhole components. This is accomplished by exposing passage 40 to allow pressure communication to the bottomhole assembly through the running tool R. The running tool R is simply removed by a pull which breaks the shear ring 68 to allow a pull-out force to remove the running tool R from the lower body L. Thereafter, the upper body U, attached to the lower end of the upper string 98, is run in the wellbore with the remaining control lines 74'. The connector self-aligns due to the action between the inclined flats 82 and 84'. The orientation sub 112 and the crossover 86 of upper body U of the connection C are free to rotate within groove 102 to facilitate this self-alignment. The control line segments 74 are made up as a result of this alignment and the male/female connection is sealed, as explained above. More than one control line connection is made up simultaneously. As the male/female components come together in a sealed relationship, their position is locked as the collet heads 104 become trapped in the groove 120 of the tubular housing 72. Further advancement of the mandrel 100 relative to the trapped collet heads 104 results in seal 62 engaging the seal bore 64 and locking ratchet mechanism 66, securing the mandrel 100 to the tubular housing 72. At this time, the production tubing is sealingly connected as the seal assembly 62 seals between the mandrel 100 and the tubular housing 72. The control line 74, one of which is shown in FIGS. 2a–c, is connected as the male and female components provide a continuous passage when sealingly connected through the boss 144 which contains the passage 80. Thus, the control line 74 requires a connection at the lower end 146 of the boss 144. The control line from the surface 74', as seen in FIG. 2a, also has a connection to upper end 116 of orientation sub 112. Thus, when the male and female components are interconnected as described above, a continuous sealed passage is formed, comprising of passages 114, 88, and 80, which extends from the upper end 116 of orientation sub 112 to the lower end 146 of boss 144.

Multiple connectors C can be used in a given string, and the control lines 74 can have outlets at different locations in the well. One of the advantages of using the connector C is that the bottomhole assembly can be run into the well and fully tested along with its associated control lines while the production tubing can be installed at a later time with the remainder of the control line back to the surface. The control line in one application can run from the surface and be connected downhole, as previously described. The control line 74 can continue through a packer through a passage such as 132. Generally speaking, the control line 74 will have a connection immediately above the packer. In multiple packer completions, since it is known what the distance between one packer and the next packer downhole is going to be, a predetermined length of control line can extend out the lower end 134 when the packer shown in FIG. 3 is sent to the wellsite. The rig personnel simply connect the control line 74 extending out the lower end 134 to the next packer below, and the process is repeated for any one of a number of packers through which the control line 74 must pass as it goes down the wellbore before making a turn to come right back up to the surface. One application of such a technique is to install fiber optic cable through the control line so that the fiber optic cable F can extend from the surface to the bottomhole assembly and back up again. Through the use of the fiber optic cable, surface personnel can determine the timing and location of temperature changes which are indicative of production of undesirable fluids. Therefore, on a real-time basis, rig personnel can obtain feedback as to the operation of downhole valves or isolation devices to produce from the most desirable portion of the well and minimize production of undesirable fluids. Fluid pressure can be used to insert or remove the fiber optic cable. There are numerous other possible uses for this technology to be used with other than fiber optic cable without departing from the spirit of the invention.

Those skilled in the art will appreciate that the orientation of the male/female components to connect the control line 74 downhole can be in either orientation so that the male component is upwardly oriented or downwardly oriented without departing from the spirit of the invention. The invention encompasses a connector which can be put together downhole and which is built in a manner so as to allow control line testing, as well as functioning of bottomhole components, without having run the upper string and its attendant control line. Thus, it is also within the scope of the invention to connect the control line to the upper string in a multitude of different ways as long as the connection can be accomplished downhole and the connection is built to facilitate the testing of the control line adjacent the bottomhole components, as well as the subsequent operation of the necessary bottomhole components, all prior to inserting the upper string. Those skilled in the art will appreciate that the preferred embodiment described above illustrates a push-together technique with an orientation feature for the control line segment of the joint. However, different techniques can be employed to put the two segments of the connector together downhole without departing from the spirit of the invention.

Any number of different pressure-actuated components can be energized from the control line 74, such as plugs, packers, sliding sleeve valves, safety valves, or the like. The control line, since it runs from the surface down to the bottomhole assembly and back to the surface, can include any number of different instruments or sensors at discrete places, internally or externally along its path or continuously throughout its length, without departing from the spirit of the invention. As an example, the use of fiber optic cable from the surface to the bottomhole assembly and back to the surface is one application of the control line 74 illustrated in the invention. Any number of control lines can be run using the connector C of the present invention. Any number of connectors C can be employed in a string where different control lines terminate at different depths or extend to different depths in the wellbore before turning around and coming back up to the surface.

The foregoing disclosure and description of the invention are illustrative and explanatory thereof, and various changes in the size, shape and materials, as well as in the details of the illustrated construction, may be made without departing from the spirit of the invention.

What is claimed is:

1. An apparatus for downhole testing, from the surface, of at least one control line adjacent a downhole tool assembly comprising:
   at least one tubular housing connectable to the downhole tool assembly, said at least one tubular housing comprising at least one exterior connection connected to said at least one control line which extends toward the downhole tool assembly;
   a running tool having an interior defined by a wall and connectable to said at least one tubular housing to allow said at least one tubular housing with said at least one control line and the downhole tool assembly to be run to a desired location downhole, said running tool in fluid communication with said at least one exterior connection through an opening in said wall so as to allow a pressure test at said desired location through said running tool of said at least one control line which extends from said at least one exterior connection.

2. The apparatus of claim 1, wherein:
said at least one exterior connection comprises one half of a male female push in connection, said running tool comprising the other half of said male female connection whereupon makeup of said male female connection, the interior of said running tool is in fluid communication with said at least one control line through said at least one exterior connection.

3. The apparatus of claim 2 further comprising:
an upper housing having the same portion of said male female connection as said running tool, said upper housing insertable downhole after removal of said running tool, said upper housing connected to a control line segment which extends from the surface to the portion of the male female connection on said upper housing, whereupon makeup of said male female connection said at least one control line extends from the surface past said at least one tubular housing and toward the downhole tool assembly.

4. The apparatus of claim 3 wherein:
said upper housing and said at least one tubular housing comprise an alignment device to insure proper orientation of each said connection before they can be pushed together downhole.

5. The apparatus of claim 4, further comprising:
a locking mechanism which engages after insertion of said male portion into said female portion of each said connection to selectively hold them together.

6. The apparatus of claim 5, wherein:
said upper housing is selectively, releasably, sealingly locked to said at least one tubular housing.

7. The apparatus of claim 1, further comprising:
at least two exterior connections on said at least one tubular housing, said at least one control line extending from one of said at least two exterior connections to or through at least part of the downhole tool assembly and terminating at another exterior connection on said at least one tubular housing, whereupon said running tool in fluid communication with said at least two exterior connections can pressure test a U-shaped portion of said at least one control line between said at least two exterior connections.

8. The apparatus of claim 7, further comprising:
at least one upper housing comprising at least one pair of control lines connected to it which extend from the surface, said at least one upper housing insertable downhole after removal of said running tool to connect said at least one pair of control lines respectively to said at least two exterior connections on said at least one tubular housing downhole so as to provide at least one continuous control line from the surface beyond said at least one tubular housing and back to the surface.

9. The apparatus of claim 8, further comprising:
at least two tubular housings spaced from each other and assembled to the downhole tool assembly;
a plurality of pairs of control lines connected from said surface to said at least one upper housing and extending to different locations downhole by a connection on at least one of said at least two tubular housings.

10. The apparatus of claim 1, further comprising:

an upper housing having at least one control line connected to it which extends from the surface, and terminates in an exterior connection, said upper housing insertable downhole after removal of said running tool, whereupon said at least one exterior connection of said at least one tubular housing and said upper housing sealingly engage downhole to extend said at least one control line from the surface past said at least one tubular housing and toward the downhole tool assembly.

11. The apparatus of claim 10, further comprising:

at least one signal transmitting cable disposed in said at least one control line extending from the surface to beyond said at least one tubular housing.

12. The apparatus of claim 11, wherein:

said upper housing comprises at least a pair of control lines extending from the surface and terminating at least a pair of external connections on said upper housing;

said at least one tubular housing comprising at least one pair of exterior connections between which extends a control line forming a generally U-shaped and extending downward toward the downhole tool assembly;

said at least one signal transmitting cable comprises a fiber optic cable extending from the surface through said at least one control line downhole and back to the surface.

13. An apparatus for downhole testing, from the surface, of at least one control line adjacent a downhole tool assembly comprising:

at least one tubular housing connectable to the downhole tool assembly, said at least one tubular housing comprising at least one exterior connection connected to said at least one control line which extends toward the downhole tool assembly;

a running tool having an interior defined by a wall and connectable to said at least one tubular housing to allow said at least one tubular housing with said at least one control line and the downhole tool assembly to be run to a desired location downhole, said running tool in fluid communication with said at least one exterior connection through an opening in said wall so as to allow a pressure test at said desired location through said running tool of said at least one control line which extends from said at least one exterior connection;

said running tool further comprises a valve which, in a closed position, facilitates pressurization of said at lest one control line and, in an open position, allows pressure to be transmitted through said at least one tubular housing to operate the downhole tool assembly.

14. The apparatus of claim 13, wherein: said running tool is sealingly engaged to said at least one housing.

15. The apparatus of claim 14, wherein:

said running tool is releasably engaged to said tubular housing.

16. A method of testing at least one control line downhole comprising:

connecting a tubular housing to a downhole tool assembly, said tubular housing having at least one external control line and at least one connection for said at least one control line;

connecting a running tool to said tubular housing;

providing fluid communication through said running tool into said external control line;

connecting tubing to said running tool;

running in said running tool on said tubing;

pressure testing the at least one external control line extending downhole from said tubular housing through said running tool.

17. The method of claim 16, further comprising:

removing the running tool;

connecting at least one upper control line with an end connection to an upper housing;

running in said upper housing and upper control line on tubing;

joining downhole said end connection on said at least one upper control line to said connection on said tubular housing.

18. The method of claim 17, further comprising:

extending a signal cable from the surface through said at least one upper control line and into said at least one external control line, extending from the tubular housing and toward the downhole tool assembly.

19. The method of claim 18, further comprising:

providing at least one pair of upper control lines each ending in an end connection externally to said upper housing;

providing said at least one control line on said tubular housing in a generally U-shape with at least a pair of connections on said tubular housing;

providing an alignment feature between said housings so as to align connections between them;

moving said housings together to selectively sealingly secure said aligned connections;

running at least one fiber optic cable as said signal cable from the surface, down through one said at least one upper control line, past said tubular housing through said at least one control line connected to it, and back to the surface through another said at least one upper control line on said upper housing.

20. A method of testing at least one control line downhole comprising:

connecting a tubular housing to a downhole tool assembly, said tubular housing having at least one external control line and at least one connection for said at least one control line;

connecting a running tool to said tubular housing;

providing fluid communication through said running tool into said external control line;

connecting tubing to said running tool;

running in said running tool on said tubing;

pressure testing the at least one external control line extending downhole from said tubular housing through said running tool;

opening a valve in said running tool after said pressure testing;

operating a portion of the downhole tool assembly through said running tool.

* * * * *